United States Patent [19]

Matsumura et al.

[11] Patent Number: 5,056,522
[45] Date of Patent: Oct. 15, 1991

[54] SUPERSONIC OPHTHALMIC MEASURING APPARATUS

[75] Inventors: Isao Matsumura, Yokosuka; Takashi Masuda, Kawasaki; Yoshimasa Hamano, Yamato; Shigeo Maruyama, Machida; Yukitsugu Nakamura, Sagamihara; Kazunobu Kobayashi, Yokohama, all of Japan

[73] Assignee: Canon Kabushiki Kaisha, Tokyo, Japan

[21] Appl. No.: 633,180

[22] Filed: Dec. 28, 1990

Related U.S. Application Data

[63] Continuation of Ser. No. 264,894, Oct. 31, 1988, abandoned.

[30] Foreign Application Priority Data

Nov. 2, 1987 [JP] Japan ................... 62-277733
Mar. 31, 1988 [JP] Japan ................... 63-79260
Jul. 22, 1988 [JP] Japan ................... 63-183335

[51] Int. Cl.$^5$ ............................................ A61B 3/16
[52] U.S. Cl. ........................ 128/645; 128/661.06; 128/662.03; 351/212
[58] Field of Search ........................ 128/645–652, 128/662.03, 661, 06; 351/208, 211, 212

[56] References Cited

U.S. PATENT DOCUMENTS

| 3,394,462 | 1/1976 | Rende ................... 128/652 |
| 4,508,121 | 4/1985 | Wyers . | |
| 4,564,018 | 1/1986 | Hutchison et al. .......... 128/661.06 |
| 4,666,269 | 5/1987 | Nakamura et al. . | |
| 4,764,006 | 8/1988 | Namano et al. . | |
| 4,766,904 | 8/1988 | Kozin et al. ............ 128/652 |
| 4,770,523 | 9/1988 | Yamada ................ 351/211 |

FOREIGN PATENT DOCUMENTS 8912424  12/1989  PCT Int'l Appl. .......... 128/661.06

Primary Examiner—Stephen C. Pellegrino
Assistant Examiner—Robin R. Longo
Attorney, Agent, or Firm—Fitzpatrick, Cella, Harper & Scinto

[57] ABSTRACT

A supersonic ophthalmic measuring apparatus includes a supersonic probe for contacting the cornea of an eye to be examined. A calculator for calculating the amount of depression of the cornea of the eye to be examined caused by the supersonic probe, and a corrector for correcting the result of the measurement of the eye axis length of the eye to be examined by the supersonic probe by the amount of depression.

13 Claims, 6 Drawing Sheets

FIG. 14
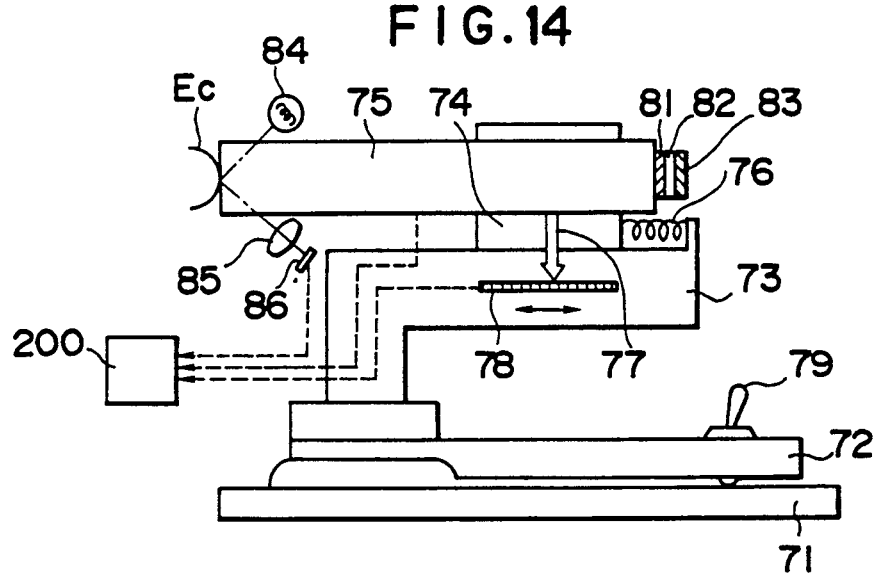
FIG. 15
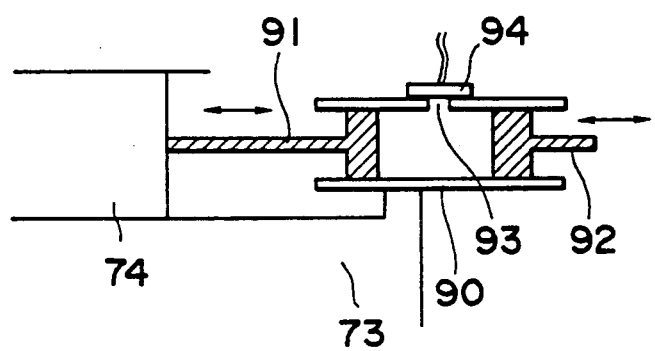
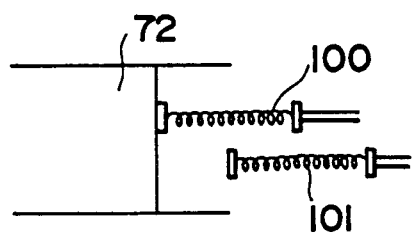
FIG. 16(a)
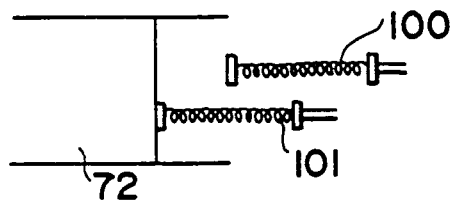
FIG. 16(b)

SUPERSONIC OPHTHALMIC MEASURING APPARATUS

This application is a continuation of application Ser. No. 264,894 filed Oct. 31, 1988, now abandoned.

BACKGROUND OF THE INVENTION

1. Field of the Invention

This invention relates to a supersonic ophthalmic measuring apparatus for measuring the distance between various regions of an eye to be examined such as the eye axis distance with a supersonic probe brought into contact with the cornea of the eye to be examined.

2. Related Background Art

There is known an apparatus of the soft type in which water is poured into a rubber bag provided at the end of a supersonic probe and the supersonic probe is brought into contact with the cornea of an eye to be examined to thereby measure the eye axis length. There is also known an apparatus using a supersonic probe of the hard type which eliminates the cumbersome operation described above. Apparatuses of this type which can measure not only the eye axis distance but also the shape proposed in U.S. Pat. No. 4,764,006 and Japanese Patent Application No. 62-51785 (corresponding to U.S. Ser. No. 162,250).

Now, where measurement is effected by the use of the conventional supersonic probe, particularly, the supersonic probe of the hard type, the cornea is deformed and as a result, the measurement of the eye axis length is inaccurate.

SUMMARY OF THE INVENTION

It is an object of the present invention to provide a supersonic ophthalmic measuring apparatus which can determine an accurate eye axis length even when a supersonic probe of the hard type is used.

It is further object of the present invention to provide an apparatus which can measure the eye axis distance of an eye to be examined as well as the shape of the cornea of the eye to be examined or the value of the eye pressure thereof.

BRIEF DESCRIPTION OF THE DRAWINGS

FIG. 14 shows the construction of a fifth embodiment of the present invention.

FIGS. 15 and 16 show the constructions of further embodiments of pressing means.

DESCRIPTION OF THE PREFERRED EMBODIMENTS

Figure 1:
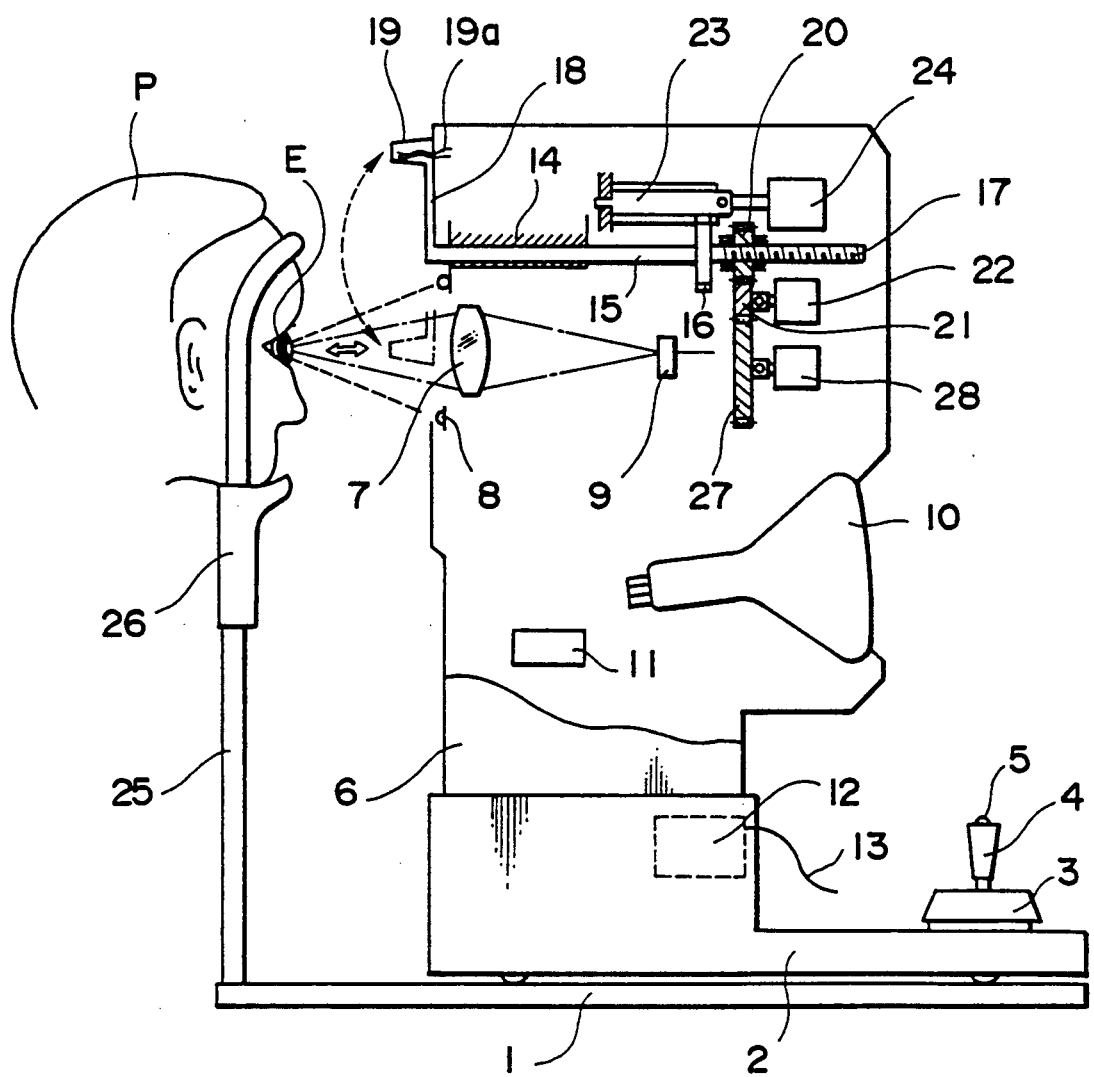
FIG. 1 shows a first embodiment of the present invention.

Referring to FIG. 1 which shows a first embodiment of the present invention, the reference numeral 1 designates a base bed and the reference numeral 2 denotes a movable bed. The combination of these constitute a sliding bed often used in an optical machine, and displaces a machine body 6 carried on the movable bed movable within a predetermined range in the direction of the left and right eyes of an examinee or in the direction of the optic axis. The reference numeral 3 designates a vertically moving ring which causes the body 6 to be vertically movable within a predetermined range by the rotation thereof. The reference numeral 4 denotes an operating rod for sliding the sliding bed in the same direction by tilting in any direction. The reference numeral 5 designates a measuring switch capable of commanding a measuring function operation by being depressed. The body 6 contains therein a major measuring funciton member including an optical system, an indicator, etc. The reference numeral 7 denotes an objective lens, and the reference numeral 8 designates light sources. A plurality of (for example, four at equal intervals) such light sources are installed around the objective lens in a predetermined relationship for the observation of the eye E to be examined or for a cornea curvature measurement which is another function.

The reference numeral 9 denotes a TV camera. When it is used also for the cornea curvature measurement, the TV camera 9 may desirably be one using a solid-state image pickup device having little electrical strain. The reference numeral 10 designates a TV monitor, the reference numeral 11 denotes a processor, the reference numeral 12 designates a printer, and the reference numeral 13 denotes printing paper.

The reference numeral 14 denotes a guide portion which holds a slidable and rotatable shaft 15. The slidable and rotatable shaft 15 is slidable axially within a predetermined range is rotatable about the axis thereof, and has a gear 16 for rotation and an externally threaded portion 17 for sliding movement, and has an arm 18 at the examinee P side and a probe 19 protruding toward the examinee side for transmitting and receiving a supersonic wave. The reference character 19a designates a cable.

The reference numeral 20 denotes a female screw whose inner side meshes with the externally threaded portion 17 and which is rotated in a predetermined position. The female screw 20 has a gear 21 formed on the outer periphery thereof, and is connected to a motor 22 through a gear 21. The gear 21 is also connected to a potentiometer 28 through a gear 27. The gear 16 meshes with a gear 23 having a long tooth width within such a range that its meshing engagement is not released even if the gear 16 slides. The gear 23 is connected to a motor 24.

The reference numeral 25 designates a strut which projects from and is provided on the base bed 1 and. Strut 25 has a face fixing stand 26 vertically movable within a predetermined range. The examinee P can have his face fixed by these. In FIG. 1, the letter E designates the eye to be examined.

Figure 2:
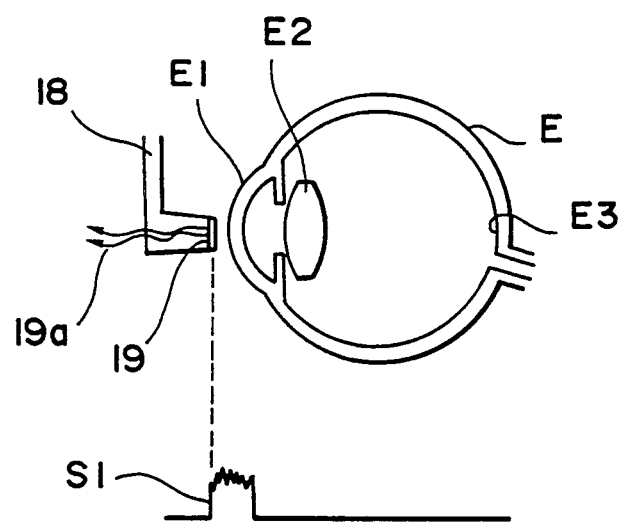
FIG. 2 shows a cross-section of an eye to be examined and a reflection signal during non-contact.
Figure 3:
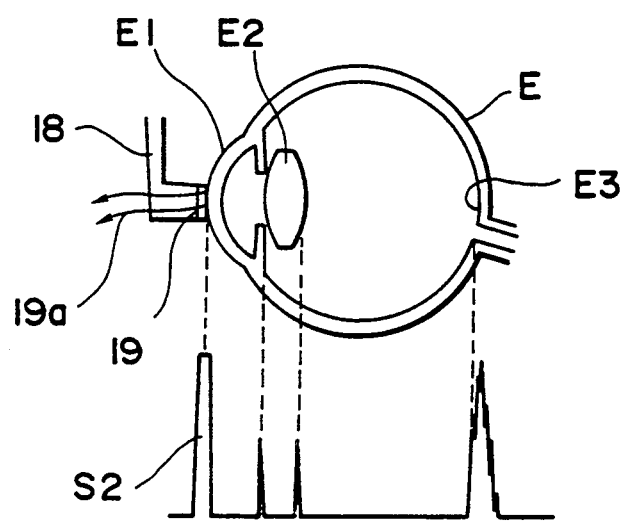
FIG. 3 shows a cross-section of the eye to be examined and a reflection signal during contact.

FIG. 2 is a cross-sectional view of the eye E to be examined and shows the eye E when the probe 19 is not in contact with the eye E, and FIG. 3 shows the eye E when the probe 19 is in contact with the eye E. E1 denotes the cornea, E2 designates the crystalline lens, E3 denotes the retina, S1 designates a reflection signal obtained from the probe 19 when it is not in contact with the eye E, and S2 denotes a reflection signal obtained from the probe 19 when it is in contact with the eye E. In S2, a remarkable reflection signal is obtained from the surface of the cornea, the front and rear faces of the crystalline lens and the retina, and it can be clearly distinguished from the multiplex reflection signal S1 from the interface between the probe itself and the air.

Figure 4:
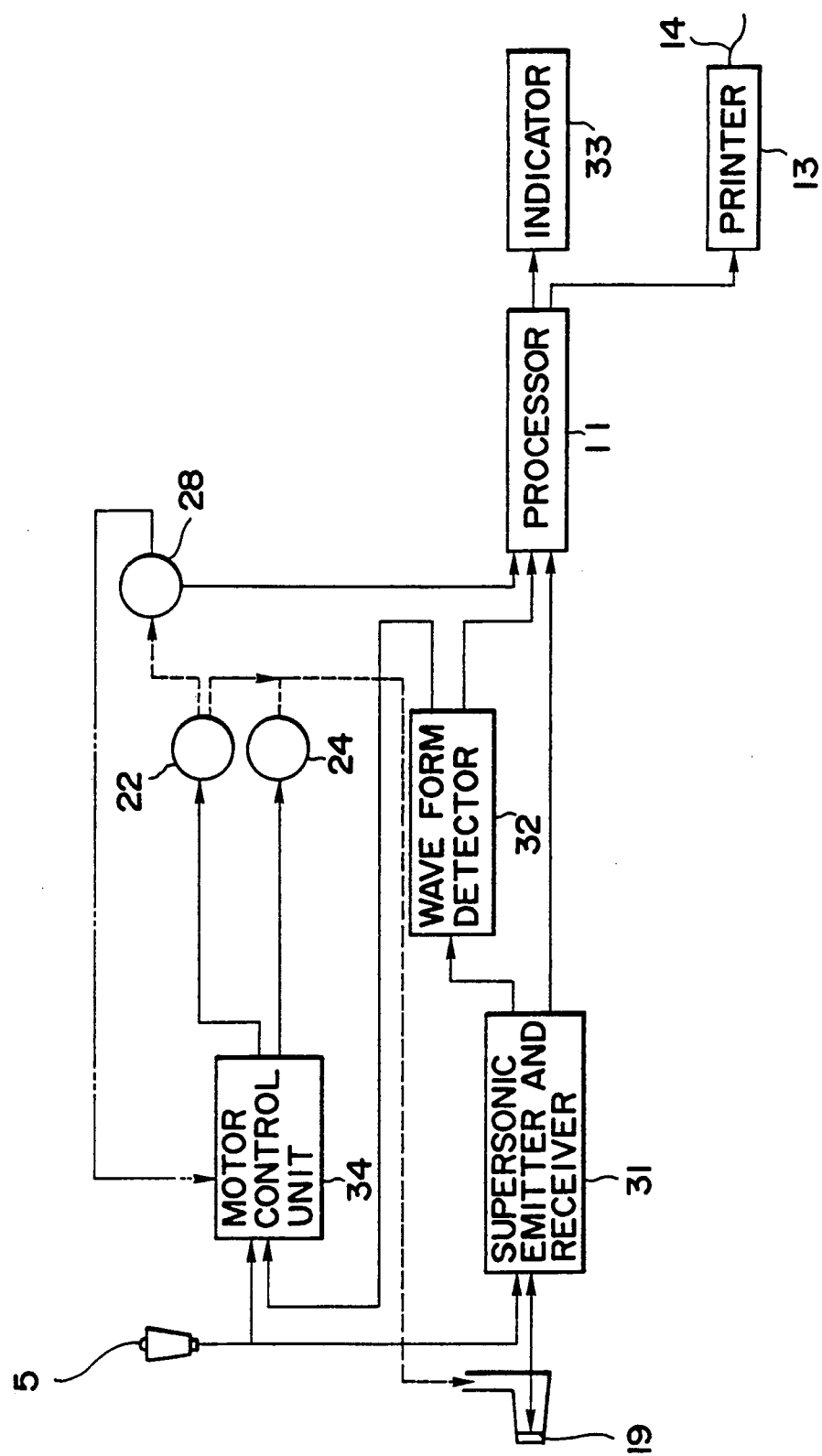
FIG. 4 is a block diagram of a processing system.

Referring now to FIG. 4 which is a block diagram of a processing system, the reference numeral 31 designates a supersonic emitter and receiver which emits a supersonic wave from the probe 19 and receives the reflected wave from E1-E3 of the eye E to be examined as previously described, on the basis of a command from the measuring switch 5. The reference numeral 32 denotes a wave form detector which discriminates the presence of the wave form S2.

The reference numeral 33 designates an indicator for indicating the result of processing by the processor 11. The indicator 33 may be a segment type light-emitting diode or the like. Alternatively, the result of the processing by the processor 11 may be indicated on the TV monitor at a corner of the display of the image of the eye E to be examined by the TV camera 9. The reference numeral 34 denotes a motor control unit which controls the motor 22 and the motor 24 on the basis of a command from the measuring switch 5, or on the basis of the output of the wave form detector 32, or on the basis of the output of the potentiometer 28.

The operation in the above-described construction will now be described. First, the examinee P has his face fixed on the face fixing stand 25. The operator tilts the operating rod 5 and rotates the vertically moving ring 3, thereby sliding the body 6 and vertically moving it. The operator effects alignment at a predetermined proper position while watching the image of the eye E to be examined illuminated by the light sources 8, picked up by the TV camera 9 through the objective lens 7 and displayed on the TV monitor 10. When the alignment is completed, the measuring switch 5 is depressed to measure the eye axis distance, whereupon the probe 19 is rendered active by the supersonic emitter and receiver 31 as previously described, while the slidable and rotatable shaft 15 is rotated by the motor 24 through the gear 23 and the gear 16 under the control of the motor control unit 34. In addition, the slidable and rotatable shaft 15 is slid to the left as viewed in FIG. 1 by the motor 22 through the gear 21, the female screw 20, and the externally threaded portion 17, whereby the probe 19 is moved from its solid-line position to its dot-and-dash line position on the optic axis of the objective lens, and further toward the eye E to be examined.

The control of the rotation of the motor 24 is accomplished by a suitable rotation stopper (not shown) or rotation detecting means (not shown) such as a potentiometer, or by a well-known method in which a stepping motor is used as the motor 24 and the pulse number applied thereto is controlled. Even if the probe 19 comes near the eye to be examined, the reflection signal before the probe contacts the eye to be examined is in the state of S1 of FIG. 2 as previously described; but when the probe comes to the contact starting position, the reflection signal assumes the state of S2 of FIG. 3. The wave form detector 32 detects the appearance of this signal S2, for example, from a variation in the pulse width of the earliest signal and stops the rotation of the motor 22 through the motor control unit 34.

It is ideal to measure the eye axis distance in the state of the contact starting position in which S2 appears, that is, the state in which the pressure of the probe 19 against the eye E to be examined is zero, but in reality, there is a mechanical delay before the probe is completely stopped, and it is necessary to correct for the influence of this mechanical delay. The processor 11 detects the position $l_1$ in the direction of sliding movement of the slidable and rotatable shaft 15 when the probe 19 is in the contact starting position wherein it contacts with the eye E to be examined, from the output of the wave form detector 32 and from the output of the potentiometer 28.

When a predetermined time has passed after the motor is completely stopped with the mechanical delay taken into account, the processor 11 again calculates the position $l_2$ in the direction of sliding movement of the slidable and rotatable shaft 15 and the eye axis length $l_p$ from the output of the potentiometer 28, and adds an amount of displacement $(l_2 - l_1)$ to the eye axis distance $l_p$ and calculates the eye axis distance $l_0$ of this eye length is provided on the indicator 33 or the eye axis length is printed out on the printing paper 14 by the printer 13.

When the detection of the position $l_2$ in the direction of sliding movement and the calculation of the eye axis length is terminated after a predetermined time has passed from the appearance of S2 in the above-described embodiment, the motor control unit 34 can reverse the motor 22 and the motor 24 so that the output of the potentiometer 28 assumes an initial value and so that the output of the rotation detecting means, not shown, likewise assumes an initial value, thereby initializing the motors.

Alternatively, any variation in the output of the potentiometer 28 may be detected instead of the lapse of a predetermined time from the appearance of S2, and use may be made of the output value of the potentiometer 28 and the eye axis distance $l_p$ at a point in time in which the variation in the output has become zero.

Figure 5:
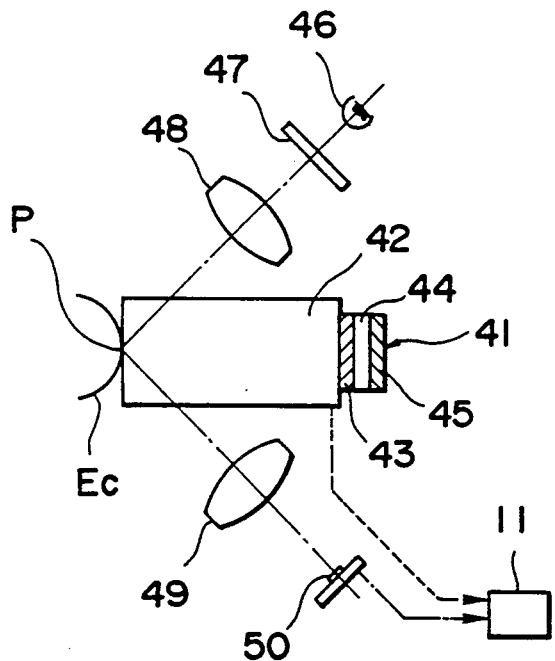
FIG. 5 shows the construction of a second embodiment of the present invention.

Referring now to FIG. 5 which shows a second embodiment of the present invention, the reference numeral 41 designates a supersonic probe in contact with the cornea Ec of the eye to be examined. This probe 41 comprises, in succession from the cornea Ec side, a light transmitting member 42, a sound adjusting layer 43, a supersonic vibrator 44 and a sound absorber 45. A light source 46 is provided obliquely above the cornea Ec, and an index plate 47 and a photo-taking lens 48 are arranged toward the cornea Ec. A projection lens 49 and a one-dimensional light receiving element 50 comprising a line-like CCD or the like are disposed in the direction of reflection from the cornea Ec.

Figure 6:
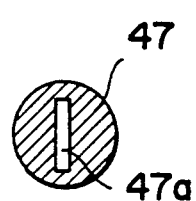
FIG. 6 is a front view of an index plate.
Figure 7:
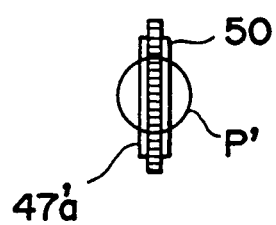
FIG. 7 illustrates an image on a light receiving element.

Measurement of the eye axis distance is effected with the supersonic probe 41 urged against the cornea Ec of the eye to be examined, and at this time, the cornea Ec and the supersonic probe 41 are in contact with each other with a contact surface P interposed therebetween. On the other hand, as shown in FIG. 6, a slit-like index mark 47a is provided on the index plate 47 illuminated by the light source 46, and this index mark 47a is projected on the contact surface P between the cornea Ec and the supersonic probe 41 through the light transmitting member 42 of the supersonic probe 41. At this time, the lengthwise direction of the index mark 47a is coincident with a direction perpendicular to the plane of the drawing sheet containing FIG. 6. The light reflected by the contact surface P is projected onto the light receiving element 50 by the projection lens 49 through the light transmitting member 42. FIG. 7 shows the state on the light receiving element 50, and the index mark 47a and the contact surface P' reflected by the end surface of the light transmitting member 42 are projected upon the light receiving element 50.

Figure 8:
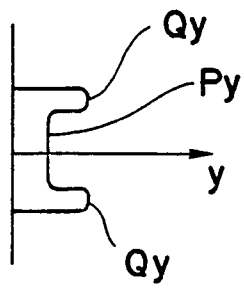
FIG. 8 shows the output wave form of the light receiving element.

Here, considering a photoelectric output y provided by the light receiving element 50, as shown in FIG. 8, the output of the contact surface portion is Py and the output of the non-contact surface portion is Qy, and the width of the contact portion can be found from these outputs Py and Qy. The reason why the photoelectric output Py is lower than the output Qy is that the refractive index of the contact surface P is small as compared with the non-contact surface portion and is reduced in reflectance. Here, if the radius of curvature of the cornea Ec is R and the width of the contact portion is D, the amount of depression x of the cornea is calculated from the following equation:

$$x = R - \{R^2 - (D/2)^2\}^{\frac{1}{2}}$$

Here, it is also possible to input a standard value as R, but if the radius of curvature of the cornea Ec of the eye to be examined is found beforehand by the use of the cornea shape measuring system (members 7, 8 and 9) shown in FIG. 1, it will become possible to calculate the exact amount of depression x for each individual.

If this amount of depression x is added to the eye axis length obtained by the supersonic probe 41, there will be found a corrected eye axis length. These calculations are accomplished by the processor 11.

Figure 9:
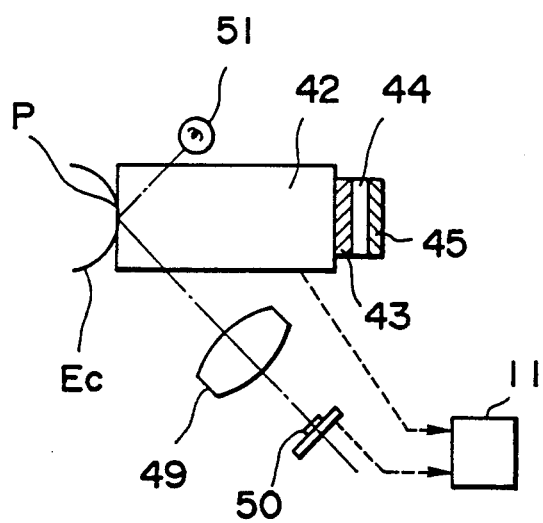
FIG. 9 shows the construction of a third embodiment of the present invention.

FIG. 9 shows a third embodiment in which the image of the contact surface P itself is picked up. In FIG. 9, reference characters similar to those in FIG. 5 designate similar members. That is, in this third embodiment, the contact surface P is illuminated by a light source 51 and this contact surface P is projected onto the light receiving element 50.

Figure 10:
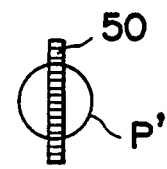
FIG. 10 illustrates an image on a light receiving element.
Figure 11:
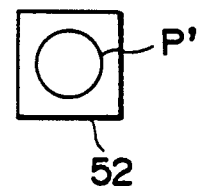
FIG. 11 illustrates an image on an area type light receiving element.

FIG. 10 shows this state, and the image P' of the contact surface is projected onto the light receiving element 50 and the width of the contact portion P is measured. In this embodiment, an area type light receiving element 52 shown in FIG. 11 may be used instead of the light receiving element 50.

Figure 12:
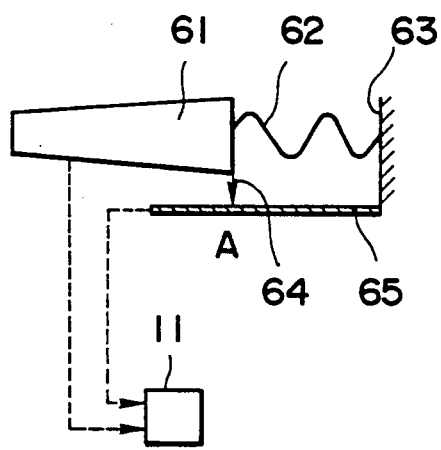
FIG. 12 shows the construction of a fourth embodiment of the present invention.

FIG. 12 shows a fourth embodiment. A supersonic probe 61 is supported by a spring 62 extending from a frame 63, and the positional relation therebetween is indicated at a position A pointed to by a needle 64.

Figure 13:
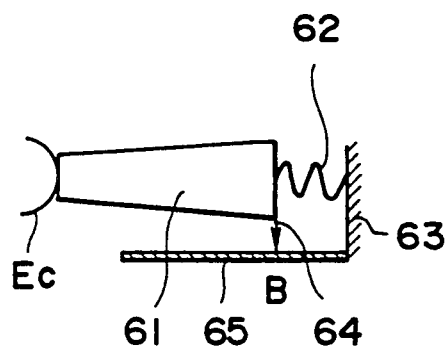
FIG. 13 is a side view showing a supersonic probe as it is in contact with the cornea.

FIG. 13 shows a state in which the eye axis length is measured with the supersonic probe 61 brought into contact with the cornea Ec of the eye to be examined, and the pressure force in this case is found by reading a position B on a scale 65 pointed to by the needle 64. That is, if the relation between the pressure force and the amount of depression of the cornea Ec is found in advance, the amount of depression can be immediately calculated. If this amount of depression is added to the eye axis length obtained by the supersonic probe 61, a corrected eye axis length can be found. These calculations are accomplished by the processor 11.

FIG. 14 show a fifth embodiment in which the embodiment illustrated in FIGS. 5 or 9 and the embodiment illustrated in FIG. 12 are combined so that the eye axis length and the eye pressure can be measured.

According to the apparatus of this embodiment, the pressure force to the cornea necessary to create a predetermined depression of the cornea which provides the standard of the eye pressure measurement (this pressure force is the value of the eye pressure) can be calculated, and as viewed from another angle, depending on how much the cornea will be depressed when a predetermined pressure is applied to the cornea, the value of the eye pressure can be found conversely by calculation. Also, according to this apparatus, the amount of depression of the cornea can be calculated and therefore, if the measurement of the eye axis by a supersonic wave is effected when this amount of depression reaches a predetermined value, the error of the depression caused by pressing can also be corrected during the measurement of the eye axis length. A description will hereinafter be provided of the depression of the cornea according to the measurement of the eye pressure being referred to as the "applanation".

In FIG. 14, a movable bed 72 is installed for movement back and forth and to the left and right on a base bed 71, and a guide member 73 adjustable in the vertical direction is provided on the movable bed 72. A supersonic probe 75 adapted to contact with the cornea Ec of the eye to be examined is mounted for sliding back and forth on the guide member 73 by a probe holder 74. The probe holder 74 is biased forward by a spring 76 and the pressure force to the cornea Ec can be read by means of a needle 77 and a scale 78. An operating lever 79 is provided on the movable bed 72 so that alignment adjustment and operation of the apparatus can be effected.

The light-transmissive supersonic probe 75 comprises, in succession from the side thereof which contacts with the cornea Ec, a sound adjusting layer 81, a supersonic vibrator 82 and a sound absorber 83, and a light source 84 is provided obliquely forwardly of the cornea Ec, and a photo-taking lens 85 and a two-dimensional light receiving element 86 are disposed on the reflection optical path with respect to the cornea Ec.

During the measurement of the eye axis length, with the supersonic probe 75 brought into contact with the cornea Ec, the eye axis length is measured by a known method with the aid of a supersonic beam produced by the supersonic vibrator 82. At the same time, the light beam from the light source 84 irradiates the cornea Ec, and the light beam that has passed through the light-transmissive supersonic probe 75 and has been reflected by the applanation surface of the cornea Ec passes through the photo-taking lens 85 to the two-dimensional light receiving element 86. The area of the applanation surface is calculated from the projected image thereof. The amount of depression X of the cornea Ec caused by the applanation is calculated roughly as $$X = R - \{R^2 - (D/2)^2\}^{\frac{1}{2}}$$

where R is the radius of curvature of the cornea Ec and D is the equivalent diameter of the applanation surface, and here, the equivalent diameter D is calculated from the applanation area. Therefore, if the radius of curvature R is pre-calculated by a keratometer, the rough value of the amount of depression X can be obtained and the measured value of the eye axis length can be corrected. These calculations are accomplished by a processor 200.

Now, during the measurement of the eye pressure, the examiner operates an operating lever 79 and further presses the cornea Ec flat by the supersonic probe 75, and the pressure force when the applanation area obtained by the aforedescribed method is a predetermined value, e.g. the equivalent diameter D=3.06 mm, is measured by the needle 77 and the scale 78. The value of the eye pressure can be calculated from the thus measured pressure force and applanation area by the processor 200.

Thus, a series of operations can be continuously performed in such a manner that the eye axis length is first measured when the pressure force against to the cornea Ec is low, whereafter the operating lever 79 is operated to measure the eye pressure. If provision is made for a mechanism for producing an alarm sound or stopping the movement of the movable bed 72 and further retracting the movable bed when a predetermined pressure force or a predetermined applanation area is exceeded during the measurement of the eye pressure, safety will be secured. If in FIG. 14, the cornea shape measuring system (members 7, 8 and 9) shown in FIG. 1 is provided, it is apparent that the shape of the cornea can also be measured.

FIG. 15 shows another embodiment of the pressing means in which air, instead of the spring 76, is utilized as means for pressing the cornea Ec. In FIG. 15, a cylindrical cylinder 90 is fixed on a guide member 73, pistons 91 and 92 are slidable in the cylinder 90, the other end of the piston 91 is fixed to a probe holder 74 and the other end of the piston 92 is operable from outside. The cylinder 90 is formed with a hole 93 in which a pressure sensor 94 is mounted from outside.

During the measurement of the eye axis length and the eye pressure, the piston 91 is pushed in and the air pressure in the cylinder 90 rises. In the stationary condition of the piston 91, the pressure force against the cornea Ec and the air pressure in the cylinder 90 become equal to each other and therefore, by measuring the air pressure by the pressure sensor 94, the value of the pressure force can be found. If the apparatus is designed such that the piston 92 is retracted when the air pressure exceeds a predetermined value, a pressure force greater than necessary can be prevented from being applied to the cornea Ec.

Referring to FIG. 16 which shows still another embodiment of the pressing means, two springs 100 and 101 are provided rearwardly of the probe holder 74, and during the measurement of the eye axis length shown in FIG. 16(*a*), the spring 100 is adapted to bias against the probe holder 74, and during the measurement of the eye pressure shown in FIG. 16(*b*), the spring 101 is adapted to bias against the probe holder 74. Generally, the pressure force against the cornea Ec is lower during the measurement of the eye axis length than during the measurement of the eye pressure and therefore, an optimum spring constant can be selected in accordance with each measurement.

We claim:

1. A supersonic ophthalmic measuring apparatus comprising:
   measuring means for measuring a distance from the cornea of an eye to be examined to a predetermined region of the eye to be examined by a supersonic wave emitted by a supersonic probe which contacts and depresses the cornea of the eye to be examined;
   calculating means for quantitatively calculating an amount of depression of the cornea of the eye to be examined caused by the supersonic probe; and
   correcting means for correcting the measurement of said measuring means by adding the amount of depression calculated by said calculating means to the distance measured by said measuring means.

2. A supersonic ophthalmic measuring apparatus according to claim 1, wherein said calculating means comprises means for detecting the size of the area of contact between the supersonic probe and the cornea of the eye.

3. A supersonic ophthalmic measuring apparatus according to claim 2, further comprising means for forming the image of said area of contact itself on a sensor.

4. A supersonic ophthalmic measuring apparatus according to claim 2, further comprising means for projecting an index mark onto said area of contact, and a means for forming a reflected image of said index mark from said area of contact on a sensor.

5. A supersonic ophthalmic measuring apparatus according to claim 2, wherein said calculating means further comprises means for detecting the radius of curvature of the cornea of the eye to be examined.

6. A supersonic ophthalmic measuring apparatus according to claim 1, wherein said calculating means calculates the amount of depression by a pressure force which presses the supersonic probe against the cornea of the eye to be examined.

7. A supersonic ophthalmic measuring apparatus according to claim 1, wherein said calculating means comprises means for detecting a position in which the supersonic probe starts to contact the cornea of the eye to be examined, and means for detecting the amount of displacement of the position of the supersonic probe during measurement from said position in which said supersonic probe starts to contact with said cornea.

8. An ophthalmic measuring apparatus according to claim 1, wherein said predetermined region is the fundus of the eye to be examined.

9. An ophthalmic measuring apparatus according to claim 1, further comprising:
   projection means for projecting an index light beam onto the cornea of an eye to be examined; and
   detecting means for detecting the corneal reflection of said index light beam.

10. An ophthalmic measuring apparatus comprising:
    projection means for projecting an index light beam onto the cornea of an eye to be examined;
    first measuring means for detecting the corneal reflection of said index light beam and measuring the shape of said index light beam and measuring the shape of the cornea;
    second measuring means for measuring a distance from the cornea of the eye to be examined to a predetermined region of the eye to be examined by a supersonic wave emitted by a supersonic probe which contacts and depresses the cornea of the eye to be examined;
    calculating means for quantitatively calculating an amount of depression of the cornea of the eye to be examined caused by the supersonic probe; and
    correcting means for correcting the measurement made by said second measuring means by adding the amount of depression calculated by said calculating means to the distance measured by said measuring means.

11. An ophthalmic measuring apparatus comprising:

first measuring means for measuring a distance from the cornea of an eye to be examined to a predetermined region of the eye to be examined by a supersonic wave emitted by a supersonic probe which contacts and depresses the cornea of the eye to be examined;

first calculating means for quantitatively calculating an amount of depression of the cornea of the eye caused by the supersonic probe;

correcting means for correcting the measurement made by said first measuring means by adding the amount of depression calculated by said first calculating means to the distance measured by said first measuring means;

applanation means for pressing the supersonic probe against the cornea of the eye to be examined;

second measuring means for measuring the area of applanation and a pressure force of the cornea of the eye to be examined pressed by said applanation means; and second calculating means for calculating the eye pressure of the eye to be examined on the basis of the output of said second measuring means.

12. An ophthalmic measuring apparatus according to claim 11, wherein said applanation means depresses the cornea by an amount, when the eye pressure is measured, which is larger than the deformation amount of the cornea when the distance from the cornea to the predetermined region of the eye is measured.

13. An ophthalmic measuring apparatus according to claim 11, further comprising:

projection means for projecting an index light beam onto the cornea of the eye to be examined; and means for detecting the corneal reflection of said index light beam and for measuring the shape of the cornea.

* * * * *

UNITED STATES PATENT AND TRADEMARK OFFICE
CERTIFICATE OF CORRECTION

PATENT NO. : 5,056,522
DATED : October 15, 1991
INVENTOR(S) : ISAO MATSUMURA, ET AL.

It is certified that error appears in the above-identified patent and that said Letters Patent is hereby corrected as shown below:

TITLE PAGE

At [56], "3,394,462 1/1976 Rende" should read -- 3,934,462 1/1976 Rende --; "Wyers" should read -- Myers --; Namano" should read -- Hamano --; and "8912424 12/1989" should read -- 89/12424 12/1989 --.

At [57], line 3, "examined. A" should read -- examined, a --.

COLUMN 1

Line 13, "eye axis distance" should read -- eye axis length --.
Line 25, "proposed" should read -- of the cornea are proposed --.

COLUMN 2

Line 27, "funciton" should read -- function --.
Line 47, "range is" should read -- range and is --.
Line 50, "protruding toward" should read -- protruding somewhat toward --.
Line 66, "base bed 1 and." should read -- base bed 1. --.

COLUMN 3

Line 50, "eye axis distance," should read -- eye axis length, --.

UNITED STATES PATENT AND TRADEMARK OFFICE
CERTIFICATE OF CORRECTION

PATENT NO. : 5,056,522
DATED : October 15, 1991
INVENTOR(S) : ISAO MATSUMURA, ET AL.

It is certified that error appears in the above-identified patent and that said Letters Patent is hereby corrected as shown below:

COLUMN 4

Line 18, "with" should be deleted.
Lines 28 and 29, "distance" should read --length--.
Line 29, "of this eye" should read -- during non-oppression. Next an indication of this eye --

Signed and Sealed this

Sixth Day of April, 1993

Attest:

STEPHEN G. KUNIN

Attesting Officer

Acting Commissioner of Patents and Trademarks